United States Patent
Aygün et al.

(10) Patent No.: US 7,981,645 B2
(45) Date of Patent: Jul. 19, 2011

(54) ENZYMATIC ASYMMETRIC DECARBOXYLATION OF DISUBSTITUTED MALONIC ACIDS

(75) Inventors: Hüseyin Aygün, Frankfurt am Main (DE); Sylvia Wojczewski, Bad Soden/Taunus (DE); Markus Kircher, Frankfurt am Main (DE); Susann Rosmus, Frankfurt am Main (DE)

(73) Assignee: BioSpring GmbH, Frankfurt (DE)

( * ) Notice: Subject to any disclaimer, the term of this patent is extended or adjusted under 35 U.S.C. 154(b) by 999 days.

(21) Appl. No.: 10/597,824

(22) PCT Filed: Feb. 4, 2005

(86) PCT No.: PCT/EP2005/001156
§ 371 (c)(1),
(2), (4) Date: Aug. 9, 2006

(87) PCT Pub. No.: WO2005/078111
PCT Pub. Date: Aug. 25, 2005

(65) Prior Publication Data
US 2010/0144010 A1 Jun. 10, 2010

(30) Foreign Application Priority Data
Feb. 13, 2004 (EP) .................................... 04003293

(51) Int. Cl.
*C12P 7/12* (2006.01)
*C12N 9/14* (2006.01)
*C12N 9/18* (2006.01)

(52) U.S. Cl. .......................... 435/146; 435/195; 435/197
(58) Field of Classification Search ........................ None
See application file for complete search history.

(56) References Cited

OTHER PUBLICATIONS

Keisuke et al. Nippon Kaghakkai Koeon Yokoshu, 2003, 83, p. 1148, Abstract.*
English translation of International Preliminary Report on Patentability for PCT Patent App. No. PCT/EP2005/001156.
Database WPI, Section Ch, Week 200007, Derwent Publications Ltd., London, GB; Class B04, AN 2000-075279, XP002282111, & JP 11 299486 A (Tosoh Corp), Nov. 2, 1999, abstract.
Database WPI, Section Ch, Week 199403, Derwent Publications Ltd., London, GB; Class B04, AN 1994-021924, XP002282112, & JP 05 328976 A (Hitachi Chem Co Ltd) Dec. 14, 1993, abstract.
Gröger, H., "Enzymatic Routes to Enantiomerically Pure Aromatic α-Hydroxy Carboxylic Acids: A Further Example for the Diversity of Biocatalysis," Adv. Synth. Catal. 2001;343(6-7):547-558.
Miyazaki, M., et al., "Cysteine188 Revealed as Being Critical for the Enzyme Activity of Arylmalonate Decarboxylase by Site-Directed Mutagenesis," Bull. Chem. Soc. Jpn. 1997;70:2765-2769.
Tereo, Y., et al., "Inversion of the Enantioselectivity of Arylmalonate Decarboxylase by Point Mutation," Chem. Listy 2003;97:488.
International Search Report for PCT Patent App. No. PCT/EP2005/001156 (Jun. 27, 2005).

* cited by examiner

*Primary Examiner* — Delia Ramirez
*Assistant Examiner* — MD. Younus Meah
(74) *Attorney, Agent, or Firm* — Shelly Guest Cermak; Cermak Nakajima LLP

(57) ABSTRACT

A process for the stereoselective decarboxylation of malonic acid derivatives with mutated decarboxylases is disclosed.

7 Claims, 7 Drawing Sheets

NcoI
atgcaacaggcaagcaccccgaccattggtatgatcgtacctcccgca
M  Q  Q  A  S  T  P  T  I  G  M  I  V  P  P  A SpeI
gctggactagtgccagccgacggcgctcgtctgtatccggatttgccgtttatcgcgtcg
A  G  L  V  P  A  D  G  A  R  L  Y  P  D  L  P  F  I  A  S BamHI
ggtttgggcctgggatccgtgactcccgaaggctatgacgcggttatagaaagcgtggtt
G  L  G  L  G  S  V  T  P  E  G  Y  D  A  V  I  E  S  V  V BclI
gatcatgctcgtcgcctgcaaaaacaggggggcagccgttgtgtctctcatgggtacctcc
D  H  A  R  R  L  Q  K  Q  G  A  A  V  V  S  L  M  G  T  S SacII
ttgtcgttctaccgcggcgccgcttttaacgcggcgctgactgtcgccatgcgtgaggct
L  S  F  Y  R  G  A  A  F  N  A  A  L  T  V  A  M  R  E  A actggcctgccgtgtactaccatgagtaccgccgtgctaaacggcctgcgtgcactgggc
T  G  L  P  C  T  T  M  S  T  A  V  L  N  G  L  R  A  L  G ClaI
gtccggcgtgtggcactggcgaccgcctatatcgatgatgttaatgaacggcttgcagcg
V  R  R  V  A  L  A  T  A  Y  I  D  D  V  N  E  R  L  A  A tttctggcggaagaatccctggtaccgacaggttgtcgtagcttaggcattaccggagta
F  L  A  E  E  S  L  V  P  T  G  C  R  S  L  G  I  T  G  V XhoI
gaagcgatggctcgagtggataccgccactctggtcgatctgtgcgtccgcgcctttgaa
E  A  M  A  R  V  D  T  A  T  L  V  D  L  C  V  R  A  F  E StyI
gcagcaccagatagcgatgggattctgttgtcgtggcggtctgcttaccttggacgca
A  A  P  D  S  D  G  I  L  L  S  C  G  G  L  L  T  L  D  A atcccggaagtcgagcgtcgcctgggtgtgccagtcgtctcaagcagtccggcgggcttt
I  P  E  V  E  R  R  L  G  V  P  V  V  S  S  S  P  A  G  F RsrII
tgggatgcggtccgtttggctggcggaggcgccaaagcacgcccgggttacggccggctt
W  D  A  V  R  L  A  G  G  G  A  K  A  R  P  G  Y  G  R  L HinDIII
tttgatgagtccggtggcagccaccatcaccatcaccatiaagcttagca
F  D  E  S  G  G  S  H  H  H  H  H  H     A

Interesting amino acid positions, based on the known substrates (better conversion), novel substrates (conversion) and thermal stability, are shown.

| Position | Amino acid Wild-type | Possible amino acid | Particularly preferred amino acid |
|---|---|---|---|
| 15 | Proline | A, G | A |
| 17 | Alanine | G, S, V, L | G |
| 19 | Leucine | A, E, Q, H | Q |
| 22 | Alanine | G, V, L | G |
| 24 | Glycine | A, S | A |
| 25 | Alanine | G, V, L | G |
| 32 | Proline | A, E, Q, H, F | Q |
| 41 | Glycine | A, E, Q, H, F | E |
| 42 | Serine | A, E, Q | A |
| 46 | Glutamic Acid | A | A |
| 47 | Glycine | A, Y | A |
| 53 | Isoleucine | A, V, L | A |
| 60 | Arginine | A, Y, E | E |
| 61 | Arginine | A, E, Q, Y, H, | Q |
| 63 | Glutamine | A, E, H, Y, S | S |
| 68 | Alanine | G, E, Q, Y, H | G |
| 74 | Glycine | A, V | A |
| 75 | Threonine | A, S, G, V | A |
| 84 | Alanine | G, E, Q, Y, H | H |
| 85 | Phenylalanine | A, S, Q, H, E | A |
| 87 | Alanine | G, E, Q, Y, H | Q |
| 94 | Arginine | A, E, Y, S, N | N |
| 103 | Threonine | A, S | A |
| 112 | Leucine | A, V, I | A |
| 116 | Glycine | A | A |
| 119 | Arginine | A, K | A |
| 121 | Alanine | G, V, L | G |
| 128 | Aspartic acid | A, E, S | A |
| 139 | Alanine | G, V, L | G |
| 142 | Serine | A, T, V | A |
| 155 | Glycine | A, E, D, Q, N | E |
| 163 | Aspartic acid | A, E, S | A |
| 165 | Alanine | G, V, L | G |
| 168 | Valine | A, I, L | A |
| 171 | Cysteine | A, S | A |
| 173 | Arginine | A, K | A |
| 178 | Alanine | G, V, L | G |
| 199 | Glutamic acid | A | A |
| 202 | Arginine | A | A |
| 203 | Arginine | A | A |
| 205 | Glycine | A | A |
| 210 | Serine | A | A |

Figure 2 (continued)

| 221 | Arginine      | A | A |
|-----|---------------|---|---|
| 222 | Leucine       | A | A |
| 224 | Glycine       | A | A |
| 225 | Glycine       | A | A |
| 227 | Alanine       | G | A |
| 229 | Alanine       | G | G |
| 230 | Arginine      | A | G |
| 238 | Aspartic acid | A | G |

Alanine (A), Glutamine (Q), Glutamic acid (E), Histidine (H), Tyrosine (Y), Phenylalanine (F), Serine (S), Asparagine (N), Glycine (G), Lysine (K), Aspartic acid (D), Asparagine (N), Isoleucine (I)

```
  1  C A T G G G T C A G A T G C A G C A G G   Sequenz1opti
  1  C A T G G G  C A  A T G C A  C A G G      Sequenz2opti 21  C T T C T A C C C C G A C C A T C G G T   Sequenz1opti
 21  C         A C C C C G A C C A T  G G T    Sequenz2opti 41  A T G A T C G T T C C G C C G G C T G C   Sequenz1opti
 41  A T G A T C G T  C C  C C  G C  G C       Sequenz2opti

61

```
321  T G T C T A C C G C T G T T C T G A A C   Sequenz1opti
321  T G ▓ T A C C G C ▓ G T ▓ C T ▓ A A C   Sequenz2opti 341  G G T C T G C G T G C T C T G G G T G T   Sequenz1opti
341  G G ▓ C T G C G T G C ▓ C T G G G ▓ G T   Sequenz2opti 361  T C G T C G T G T T G C T C T G G C T A   Sequenz1opti
361  ▓ C G ▓ C G T G T ▓ G C ▓ C T G G C ▓ A   Sequenz2opti 381  C C G C T T A C A T C G A C G A C G T T   Sequenz1opti
381  C C G C ▓ T A ▓ A T C G A ▓ G A ▓ G T T   Sequenz2opti 401  A A C G A A C G T C T G G C T G C T T T   Sequenz1opti
401  A A ▓ G A A C G ▓ C T ▓ G C ▓ G C ▓ T T   Sequenz2opti 421  C C T G G C T G A A G A A T C T C T G G   Sequenz1opti
421  ▓ C T G G C ▓ G A A G A A T C ▓ C T G G   Sequenz2opti 441  T T C C G A C C G G T T G C C G T T C T   Sequenz1opti
441  T ▓ C C G A C ▓ G G T T G ▓ C G T ▓▓▓▓   Sequenz2opti 461  C T G G G T A T C A C C G G T G T T G A   Sequenz1opti
461  ▓ T ▓ G G ▓ A T ▓ A C C G G ▓ G T ▓ G A   Sequenz2opti 481  A G C T A T G G C T C G T G T T G A C A   Sequenz1opti
481  A G C ▓ A T G G C T C G ▓ G T ▓ G A ▓ A   Sequenz2opti 501  C C G C T A C C C T G G T T G A C C T G   Sequenz1opti
501  C C G C ▓ A C ▓ C T G G T ▓ G A ▓ C T G   Sequenz2opti 521  T G C G T T C G T G C T T T C G A A G C   Sequenz1opti
521  T G C G T ▓ C G ▓ G C ▓ T T ▓ G A A G C   Sequenz2opti 541  T G C T C C G G A C T C T G A C G G T A   Sequenz1opti
541  ▓ G C ▓ C C ▓ G A ▓▓▓▓▓▓ G A ▓ G G ▓ A   Sequenz2opti
```

Fig. 4-2

```
561  T C C T G C T G T C T T G C G G T G G T    Sequenz1optir
561  T ▓ C T G ▓ T G T C ▓ T G ▓ G G ▓ G G T    Sequenz2optir 581  C T G C T G A C C C T G G A C G C T A T    Sequenz1optir
581  C T G C T ▓ A C C ▓ T G G A C G C ▓ A T    Sequenz2optir 601  C C C G G A A G T T G A A C G T C G T C    Sequenz1optir
601  C C C G G A A G T ▓ G A ▓ C G T C G ▓ C    Sequenz2optir 621  T G G G T G T T C C G G T T G T T T C T    Sequenz1optir
621  T G G G T G T ▓ C C ▓ G T ▓ G T ▓ T C ▓    Sequenz2optir 641  T C T T C T C C G G C T G G T T T C T G    Sequenz1optir
641  ▓▓▓▓▓▓ T C C G G C ▓ G G ▓ T T ▓ T G     Sequenz2optir 661  G G A C G C T G T T C G T C T G G C T G    Sequenz1optir
661  G G A ▓ G C ▓ G T ▓ C G T ▓ T G G C T G    Sequenz2optir 681  G T G G T G G T G C T A A A G C T C G T    Sequenz1optir
681  G ▓ G G ▓ G G ▓ G C ▓ A A A G C ▓ C G ▓    Sequenz2optir 701  C C G G G T T A C G G T C G T C T G T T    Sequenz1optir
701  C C G G G T T A C G G ▓ C G ▓ C T ▓ T T    Sequenz2optir 721  C G A C G A A T C T G G T G G T T C T C    Sequenz1optir
721  ▓ G A ▓ G A ▓ T C ▓ G G T G G ▓▓▓▓▓ C    Sequenz2optir 741  A C C A C C A C C A C C A C C A C T A      Sequenz1optir
741  A C C A ▓ C A C C A ▓ C A C C A ▓ T A A    Sequenz2optir
```

Figure 4-3    various bases are highlighted

ENZYMATIC ASYMMETRIC DECARBOXYLATION OF DISUBSTITUTED MALONIC ACIDS

In the chemical-pharmaceutical industry, the problem that certain substances have to be used as pure substances, i.e. as nonracemic mixtures, is increasingly occurring. In some cases, however, there are no simple synthesis strategies for this type of syntheses. For this reason, in recent years, a whole series of very different enzymes which often prefer a certain substrate stereoselectively and regioselectively in their reaction were used, so that some reactions only become economically expedient through the use of enzymes.

In the case of α-substituted malonic acid derivatives, in particular aromatic derivatives or derivatives associated therewith by conjugation, there is still only a very limited range of enzymes available. Thus, for example, no simple, heterologously expressible enzyme has been described to date which accepts aromatic α-hydroxymalonic acids/tartronic acid or •-hydroxymalonic acids/tartronic acid associated therewith by conjugation and derivatives thereof or which can be used for a simple reaction. The decarboxylation can be represented schematically as follows:

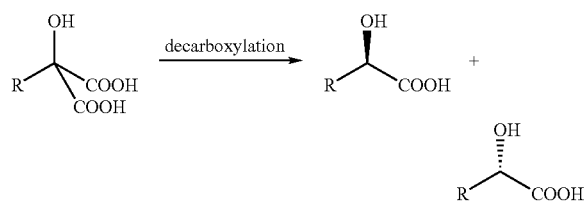

A number of enzymatic routes which, however, differ fundamentally from the synthesis route disclosed here have been described to date for the synthesis of aromatic α-hydroxycarboxylic acids. There are various known possibilities regarding the preparation of enantiomerically pure aromatic α-hydroxycarboxylic acids by an enzymatic route [Gröger, A (2001): Adv. Synth. Catal. 343, 547-558].

All known approaches to the enzymatic synthesis of α-hydroxycarboxylic acids have the disadvantage that either HCN has to be used or frequently a theoretical maximum yield of only 50% is achievable or additionally reduction equivalents have to be regenerated.

Common to all processes is that the starting substance used is never a dicarboxylic acid which is then asymmetrically decarboxylated in a targeted manner so that only one enantiomer of the sought compound forms.

The individual previously known synthesis strategies are typically presented below briefly:

Various routes start from racemic mixtures of α-OH esters or O-acetylated cyanohydrins, which are then selectively hydrolyzed. For the O-acyl-protected mandelic esters, for example, the penicillin amidase from *Alcaligenes faecalis* is used if the (S)-enantiomer is to be produced [C. Fuganti, C. M. Rosell, S. Servi, A. Tagliani, M. Terreni, Tetrahedron: Asymmetry 1992, 3, 383]. (R)-enantiomers of bulky carboxylic esters are on the other hand easily obtainable by means of a protease from *Aspergillus oryzae*. The corresponding products frequently have to be further purified by crystallization in order to obtain higher product purity.

With the use of O-acyl-cyanohydrins, use is made of the circumstance that the nondeacylated cyanohydrins can be easily converted into the corresponding carboxylic acids without changing the optical rotation of the compound. It is thus possible to start from racemic mixtures of O-acyl-cyanohydrins, which are then selectively hydrolyzed with corresponding lipases (e.g. from *Pseudomonas* spec. or *Arthrobacter* spec.).

A further synthesis route starting from racemic cyanohydrins consists in the possibility of hydrolyzing the cyanohydrins directly enantioselectively by means of nitralases, for example from *Rhodococcus*, which leads to a simpler synthesis strategy since the enantiomerically pure carboxylic acid forms in a first step. Since this strategy too is based on resolution of a racemic mixture, the maximum yield is likewise limited to 50%.

A similar but reverse route is used for the enantioselective synthesis of cyanohydrins. Starting from the aldehyde (e.g. benzaldehyde), an enzyme-catalysed hydrocyanic acid addition is carried out by means of oxynitrilases, giving the corresponding cyanohydrins (e.g. mandelonitrile). Often the reaction conditions which permit an enantiomerically pure reaction are decisive.

For the synthesis strategies carried out to date, however, a modification of the starting substance (esterification of the OH function or of the carboxyl function) is always first necessary in order subsequently to be able to separate the enantiomers. The other synthesis strategies use or produce hydrocyanic acid, which in turn represents a substantial limitation in the feasibility.

A further route to α-hydroxycarboxylic acids is the enantioselective reduction of prochiral α-ketocarboxylic acid or of the corresponding esters by means of dehydrogenases. Unless whole cells are used, the use of dehydrogenases must be coupled with a further system regenerating reduction equivalents, which once again greatly limits the possibilities of use. In order to avoid the consumption of reduction equivalents from occurring as a limitation coupled enzyme/redox processes in which the reduction equivalents consumed are enzymatically regenerated are also often used.

The stereoselective synthesis disclosed here describes a novel route. Starting from a malonic acid derivative a carboxyl group is enzymatically eliminated so that only one enantiomer is produced. This synthesis strategy has the major advantage that neither must the starting substances be first esterified nor must the desired carboxylic acids first be converted into cyanohydrins (use of HCN). Moreover, it is at least theoretically possible to achieve a product yield of 100%.

Ohta [Advances in Biochemical Engineering/Biotechnology, Vol. 63, Pages 1-29, Springer Verlag (1999)] describes an enzyme [arylmalonate decarboxylase (AMDase)] from *Alcaligenes bronchisepticus* KU1201, which decarboxylates α-methylphenylmalonic acids asymmetrically to give the corresponding phenylacetic acid derivatives.

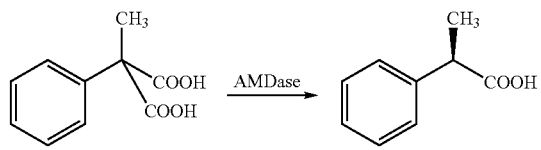

With the aid of mutants Ohta found that the cysteine residues, in particular the residue at position 188, are involved in the catalysis. In these experiments, four cysteine residues at positions 101, 148, 171 and 188 were replaced by serine residues.

In the present Application the selective modification of the enzyme arylmalonate decarboxylase (AMDase) by genetic engineering is disclosed. By means of the disclosed mutations, it is possible also to produce aromatic tartronic acid derivatives in high yield and with a high enantiomeric excess by asymmetric decarboxylation. It is therefore possible to use the mutated enzymes to decarboxylate substrates which cannot be decarboxylated with the wild-type enzyme.

The mutated decarboxylases disclosed can convert substrates with a substantially higher enzyme activity. This is of considerable importance for industrial use.

In a further aspect of the present invention, those mutated decarboxylases are disclosed which moreover have a significant improvement in the thermal stability, which in particular substantially increases the industrial applicability of the enzyme according to the invention as biocatalysts.

The present invention therefore relates to a process for the stereoselective decarboxylation of malonic acid derivatives of the formula (I)

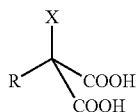

(I)

in which X has the meaning OH, SH, C2-C10 alkyl, C1-C10 alkoxy or NH$_2$ and R has the meaning aryl, heteroaryl, condensed aryl and condensed heteroaryl radical which may be optionally substituted by alkyl, alkenyl or alkynyl radicals or halogens. In the context of the present application, aryl radicals are understood as meaning aromatic hydrocarbon radicals, such as, for example, the phenyl, naphthyl or anthryl radical, which are associated with the prochiral centre either directly, by heteroatoms or by conjugation (for example via alkenediyls or alkynediyls). Heteroaryl radicals are aromatic hydrocarbon radicals which, in addition to carbon atoms may also contain heteroatoms, in particular nitrogen, oxygen or sulphur. The furyl, pyrrolyl, thiophenyl, pyrazolyl, imidazolyl, pyridinyl, pyridazinyl, pyrimidinyl, pyrazinyl, indolyl, purinyl, quinolinyl, benzofuranyl, carbazolyl, benzothiophenyl, isoquinolinyl, quinoxalinyl, pteridinyl, thiazolyl, oxazolyl or acridinyl radicals may be mentioned here by way of example. These aromatic radicals can optionally also be substituted in various positions by halogens, alkyl, alkenyl, alkynyl or alkoxy radicals. The reaction with a decarboxylase results in the formation of a compound of the formula (II)

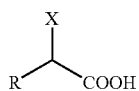

(II)

in which X and R have the abovementioned meaning.

In a preferred embodiment, the decarboxylases disclosed open up an important route to the significant class consisting of the chiral substituted acetic acids. These include, for example, in particular those compounds which, in addition to different substituents on the aromatic ring system, may contain substituted phenyl, naphthyl, furyl and thiofuryl ring systems. Exemplary structures are shown below:

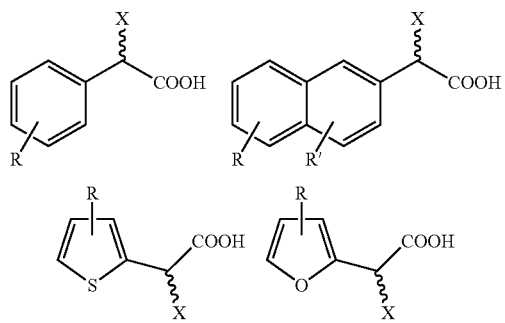

here, R and R' represent a substituent of the aryl radicals.

The malonic acid derivatives (formula I) either can be directly synthesised from malonic acid or are obtainable by carboxylation of the corresponding monocarboxylic acids. In a further aspect, the present invention relates to decarboxylases containing an amino acid sequence corresponding to SEQ ID NO:1, which has at least one mutation compared with SEQ ID NO:1, the mutation being present at one of the following amino acid positions: 17, 19, 22, 24, 25, 32, 41, 42, 46, 47, 53, 60, 61, 63, 68, 74, 83, 84, 85, 87, 94, 103, 105, 112, 116, 119, 121, 139, 142, 155, 168, 171, 173, 178, 199, 201, 202, 203, 204, 205, 210, 221, 222, 224, 225, 226, 227, 228, 229, 230, 235, 238, 239 and/or 240, the amino acid stated at the amino acid position in SEQ ID NO:1 being replaced by any other amino acid, with the proviso that, at position 188, the cysteine residue may not be replaced by other amino acids and insertion and/or deletion mutants, and not more than 10 amino acids in each case may be inserted into and/or deleted from the sequence according to SEQ ID NO:1.

By mutation of certain amino acid residues found according to the invention, it is possible to provide decarboxylase variants which are now also capable of asymmetrically decarboxylating novel substrate groups, such as, for example, α-C$_{2-10}$-alkyl-, α-hydroxy-, α-thiol- and α-aminophenylmalonic acids and the derivatives thereof. This innovation opens up a valuable route to chiral α-alkyl-, α-hydroxy-, α-thiol- and α-aminophenylacetic acid as well as derivatives thereof. Preferred exemplary product structures are shown below:

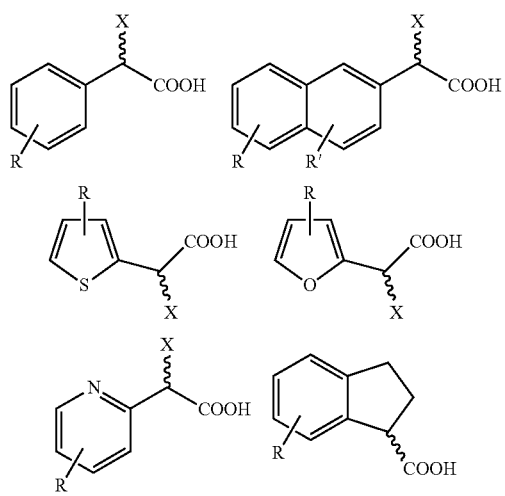

In general: 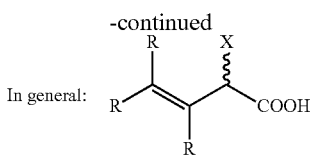

X: alkyl, OH, NH₂ and SH; R: Halogen, alkyl, alkenyl, alkinyl, aryl, thioether and ether.

Preferred decarboxylases are those which have an amino acid sequence with at least one mutation compared with SEQ ID NO:1, in which the mutation is present at the following amino acid positions: 17, 19, 24, 32, 41, 42, 46, 47, 53, 60, 61, 63, 68, 74, 84, 85, 87, 94, 103, 116, 119, 142, 171, 199, 202, 210, 225, 229, 230 and/or 238; those decarboxylases having a mutation at one of the following positions are particularly preferred: 19, 24, 32, 42, 46, 47, 60, 61, 63, 68, 84, 85, 103, 199 and/or 202, the amino acid stated at this position in SEQ ID NO:1 being replaced by glycine or alanine.

In a further aspect of the present invention, it was surprisingly found that the thermal stability of the decarboxylase according to the invention can be substantially improved by special mutations. Improved thermal stability is obtained in particular when the amino acid stated in SEQ ID NO:1 at positions 15, 32, 74, 75, 128, 163, 165 and/or 171 is replaced by alanine or glycine.

The enzyme-specific parameters, such as optimum pH and optimum temperature, were determined and published by Miyamoto & Ohta [Miyamoto K. & Ohta, H. (1992: Eur. J. Biochem. 210, 475-481)]. For determining the substrate specificity of the isolated AMDase Ohta et al. carried out a number of investigations in which the accepted substrates and the specificity of the enzyme were clearly demonstrated.

Ohta et al. were also able to show that the resulting compounds have a (R)-configuration. If, however, glycine 74 is mutated to a cysteine and at the same time the active cysteine 188 is mutated to a serine, the product configuration is changed and (S)-configured compounds then form (Terao, Y. et al., Chem. Listy 97, 488 (2003)). This effect can also be achieved if certain amino acids which neighbour glycine 74 are mutated to a cysteine. If both positions (74 and 188) are used with cysteine side chains, the result is a decarboxylase which converts the starting compounds into monocarboxylic acids at a different rate. Ohta et al. also describe a number of further mutations of the other cysteines in the enzyme, which lead to a change in the reaction rates of AMDase, based on the phenylmalonic acid and derivatives thereof. However, substrates other than α-methylarylmalonic acid and no arylmalonic acids further substituted on the α-carbon atom (simply the introduction of an α-ethyl function leads to a break down in the enzyme activity) have been reacted to date.

In a further aspect, the present invention therefore also relates to decarboxylases in which a cysteine residue at position 188 of SEQ ID NO:1 is not mutated and which, in the stereoselective decarboxylation, lead to compounds of the formula (II) which have the R-configuration.

In a further embodiment, the present invention relates to decarboxylases which, when used, form compounds of the formula (II) having the S-configuration. In the case of these decarboxylases, an amino acid between positions 69 and 81 of SEQ ID NO:1 is replaced by a cysteine and at the same time the cysteine residue at position 188 is replaced by an amino acid other than cysteine.

A further preferred embodiment discloses decarboxylases according to the invention with substantial improvement of the conversion of malonic acid derivatives of the formula (III)

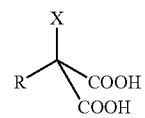

to compounds of the formula (IV)

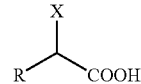

in which X has the meaning F, CH, or H and R has the meaning of substituted and unsubstituted aryl, heteroaryl, condensed aryl and condensed heteroaryl radical, it being possible for the substituents to be a halogen, alkyl, alkenyl or alkynyl radical.

In the case of these decarboxylases, at least one of the amino acids stated in SEQ ID NO:1 at position 17, 19, 22, 25, 32, 41, 42, 47, 53, 60, 61, 63, 68, 74, 84, 85, 87, 94, 103, 112, 119, 121, 139, 142, 155, 168, 173, 178, 199, 201, 203, 205, 207, 210, 221, 222, 223, 224, 225, 226, 227, 228, 229, 230, 231, 232, 238 and/or 240 is replaced.

The decarboxylases according to the invention may have further amino acids at the C-terminus and/or at the N-terminus. These additional amino acid sequences may be those which have formed as a result of cloning or which have advantages in the preparation, purification or use. The addition of a polyhistidine sequence (Hexa-his) at the C- or N-terminus permits purification of the enzyme. However, it is also possible to incorporate a leader sequence before the gene coding for the mutated decarboxylase into the vector. As a result, the enzyme can be easily removed from the host cell after expression, and improved producibility of the enzyme is thus possible. Alternatively, it is also possible to attach to the C- or N-terminus of the decarboxylase those structures which result in the enzyme remaining associated with the cell wall of the host organism after expression, so that it is possible to use, as biocatalysts, host organisms which carry decarboxylases according to the invention on the cell surfaces.

The decarboxylases according to the invention can be prepared in a preferred manner with the aid of recombinant techniques. For this purpose, a vector which contains the required constituents for expression of a foreign nucleotide sequence is usually introduced into a suitable host organism. The vector contains, at a suitable site, the polynucleotide sequence with SEQ ID NO:2 and the base exchanges coding for the mutation or the mutations. It is furthermore possible for the host organism to contain the gene, optionally with suitable regulation elements, such as, for example, promoter, etc., integrated in the chromosome. It is also possible for the host organism to contain the foreign gene integrated both in the vector and in the chromosome.

Depending on the intended use, host organism and vector, the decarboxylase can be expressed in the cytoplasmic space of the host organism, transported into the periplasmic space or discharged from the cell into the surrounding medium. The decarboxylases according to the invention can then, if required, be purified by customary purification methods, the degree of purity depending on the intended use.

For the expression of the decarboxylases according to the invention, it is possible to use customary host organisms, such as, for example, *Escherichia coli, Bacillus subtillis, Saccha-* romyces cerevisiae, Hansenula spec., Pichia pastoria or other prokaryotic or eukaryotic expression systems. The decarboxylases according to the invention are preferably expressed in *Escherichia coli*.

A further aspect of the present invention relates to transformed host organisms which can express the decarboxylases according to the invention. Depending on the intended use, it is possible to use the whole transformed host cells for the decarboxylation. However, it is also possible to use digestions or lysates or storage forms (e.g. dried cells) of these cells which contain the decarboxylase. Some of these digestions may be purified. Furthermore, it is possible to couple the decarboxylases to solid substrates in order to provide biocatalysts for the continuous reaction. The decarboxylases can preferably be coupled to column material or enclosed in polymers. The substrates can then be fed in liquid form through the columns containing the decarboxylases according to the invention, and the stereoselectively decarboxylated products can be purified after passage through the column.

The present invention therefore discloses
a) the modification of the enzyme AMDase from *Alcaligenes bronchisepticus* KU1201 by genetic engineering so that, in addition to a substantially improved conversion of the substrates known to date, aromatic tartronic acid derivatives can also be produced in high yield and with a high enantiomeric excess for asymmetric decarboxylation,
b) an optimised DNA sequence which leads to substantially improved expression of the enzyme,
c) numerous enzyme mutants which have not been previously described and which can convert the substrates with a substantially higher enzyme activity, and
d) mutations which significantly improve the thermal stability of the enzyme and thus, with the above advantages, increase the industrial usability of the enzyme as a biocatalyst.

The arylmalonate decarboxylases according to the invention (AMDase, E. C. 4.1.1.76) which are mutated compared with SEQ ID NO:1 meet the requirements for an industrially usable enzyme. It can be easily expressed heterologously in simple microorganisms and, in contrast to many decarboxylases described to date this enzyme requires no coenzyme in order to bring about a selective decarboxylation, because a cysteine side chain is used as an active residue. This AMDase accepts not only aromatic malonic acid derivatives. Certain substituents in the aromatic ring system, and α-methyl as well as some α-halides, are also tolerated as a substrate. Derivatives which carry a hydroxyl, thiol, alkyl (except for methyl) or amino function on the α-carbon atom are not converted by the wild-type enzyme described by Ohta.

DESCRIPTION OF THE FIGURES

FIG. 1 shows the wild-type amino acid sequence of the arylmalonate decarboxylase from Alcaligenes bronchisepticus (SEQ ID NO:1) and the nucleotide sequence coding for it (SEQ ID NO:2).

FIG. 2 shows the preferred amino acid exchanges. The respective positions refer to the amino acid sequence as shown in SEQ ID NO:1. The second column shows that amino acid which occurs in the wild-type sequence. In the third column, those amino acids which are preferably used instead of the amino acid occurring in the wild-type are named in the single-letter code. The fourth column (far right) shows those amino acids which, in a particularly preferred embodiment, are used in the respective position instead of the wild-type amino acid in the enzyme modified according to the invention.

FIG. 4 shows a nucleic acid sequence.

Figure 3:
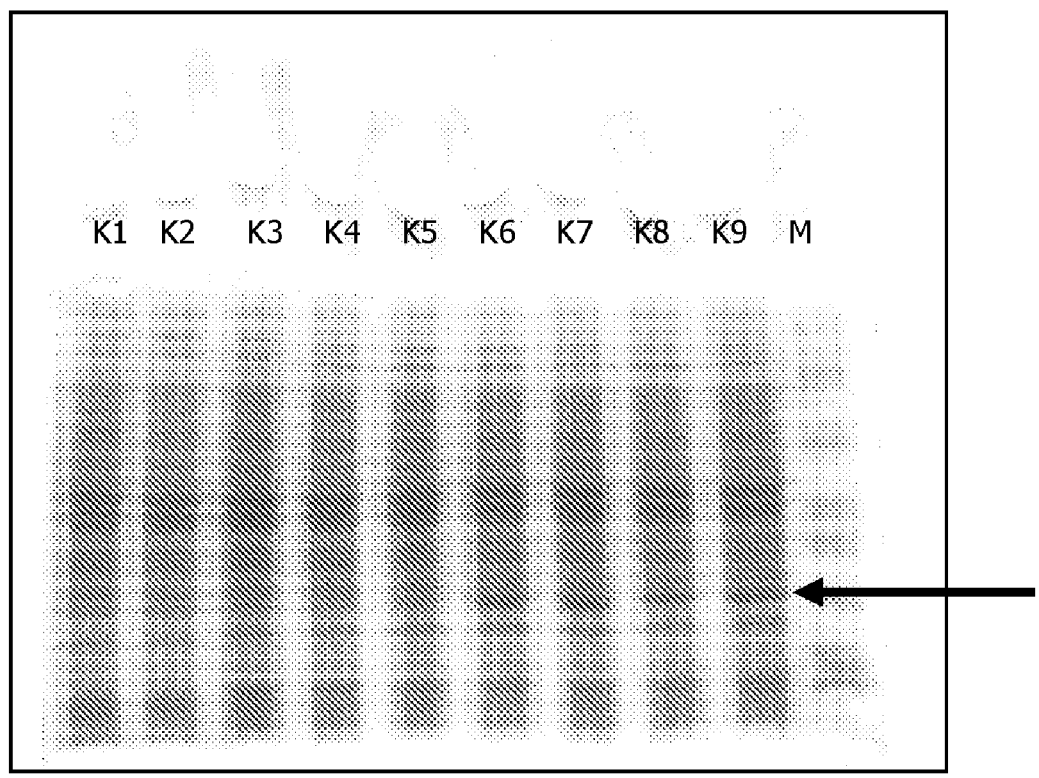
FIG. 3 shows an image of proteins in polyacrylamide gel.

The amino acid exchanges lead to the following advantages: better conversion for already known substrates; conversion of novel substrates, i.e. of those substrates which are not converted by the wild-type enzyme, and improvement of the thermal stability.

The decarboxylases according to the invention have at least one amino acid exchange. However, it is certainly preferable if a plurality of amino acids, i.e. at least two or three, in particular cases even more, amino acids, are simultaneously exchanged.

The present invention is further explained by the following examples.

EXAMPLE 1

Cloning of AMDase

The wild-type DNA sequence of arylmalonate decarboxylase from *Alcaligenes bronchisepticus* was synthesised by genetic synthesis in a sequence codon-optimized for *E. coli*. The sequence is shown in the sequence protocol of SEQ ID NO:2

```
atgcaacaggcaagcaccccgaccattggtatgatcgtacctcccgcagc tggactagtgccagccgacggcgctcgtctgtatccggatttgccgttta tcgcgtcgggtttgggcctgggatccgtgactcccgaaggctatgacgcg gttatagaaagcgtggttgatcatgctcgtcgcctgcaaaaacagggggc agccgttgtgtctctcatgggtacctccttgtcgttctaccgcggcgccg cttttaacgcggcgctgactgtcgccatgcgtgaggctactggcctgccg tgtactaccatgagtaccgccgtgctaaacggcctgcgtgcactgggcgt ccggcgtgtggcactggcgaccgcctatatcgatgatgttaatgaacggc ttgcagcgtttctggcggaagaatccctggtaccgacaggttgtcgtagc ttaggcattaccggagtagaagcgatggctcgagtggataccgccactct ggtcgatctgtgcgtccgcgcctttgaagcagcaccagatagcgatggga ttctgttgtcgtgtggcggtctgcttaccttggacgcaatcccggaagtc gagcgtcgcctgggtgtgccagtcgtctcaagcagtccggcgggcttttg ggatgcggtccgtttggctggcggaggcgccaaagcacgcccgggttacg gccggcttttttgatgagtccggtggcagc
```

The genes were synthesised via restriction/ligation cloning in the plasmid pUC19 between the interfaces EcoRI and HindIII. For this purpose, the DNA sequence was provided with a short linker fragment with the sequence 5'-ccggaattc-ccatgggccaa-3' (SEQ ID NO:3), which contains the EcoRI and the NcoI interface, at the 3' end, and with a linker of the sequence 5'-caccatcaccatcaccattaagctt-3' (SEQ ID NO:4) at 5'. The linker at the 5' end simultaneously contains the codon for six histidines in addition to the HindIII interface, so that the decarboxylase can be obtained by one-step purification by means of metal affinity chromatography.

For the cloning of the total sequence, the individual strands were synthesised by the phosphoamidite method and phosphorylated under standard condition according to the manufacturer's instructions (New England Biolabs) with T4-polynucleotidekinase. After hybridization of the individual strands to give the corresponding DNA double strands, the fragments were combined to give the total gene. Nucleotide sequence and amino acid sequences are shown in FIG. 1.

The sequence was checked by sequencing of the cloning plasmid. For expression of the arylmalonate decarboxylase (AMDase), the DNA sequence was transferred to the pBAD vector (Invitrogen) (Ncol/HindIII) and introduced into *E. coli* cells (strain: TOP10). The expression was effected by induction of the bacterial cells, at an optical density of ~0.6 (600 nm), with 0.02% L-arabinose for 8 to 15 h at 37° C. Longer induction also does not lead to the formation of insoluble protein in the form of inclusion bodies but further increases the yield of soluble enzymes.

EXAMPLE 2

Provision of AMDase 2.1 Fermentation of AMDase

The fermentation of the individual mutants as well as of the wild-type protein was effected in LB medium with carbenicillin (200 µg/ml) as an antibiotic (however, ampicillin in the same concentration could also be used for the laboratory fermenter). The culture of the bacterial cells (TOP10) is effected in 500 ml shaking flasks (200 ml of culture liquid) or 5 l flasks (1 l of culture liquid) at 37° C. at about 300 rpm. For expression of the proteins, the cells are induced with 0.02% (L)-arabinose and shaken further at 37° C. The protein expression can be both started at 0.6 $OD_{600}$ and begun directly with inoculation of the flasks. The individual cultures were induced as a rule for at least 4-6 h.

From 200 ml of shaken culture, it is possible to isolate between 5 and 150 mg of purified AMDase per litre of culture medium, depending on mutation, medium and induction time.

The AMDase-expressing cells can, however, also be cultured in the laboratory fermenter.

From a 4 litre LB fermentation (pH controlled, gassed with compressed air, about 800 rpm stirring speed, about 15 h culture at 37° C., induction on inoculation with 0.02% L-arabinose), it is possible to isolate about 60 mg of purified protein per litre. If the cells are cultured correspondingly in TB/glycerol medium in the fermenter (pH controlled, gassed with compressed air, about 800 rpm stirring speed, about 15 h culture at 37° C., induction on inoculation with 0.02% L-arabinose), it is easily possible to purify up to 240 mg of enzyme per litre of culture medium.

In comparison, Ohta gives a yield of 1800 units/litre of culture medium (TB medium), which corresponds to a yield of almost 5 mg of pure enzyme per litre (377 units/mg of protein) [Ohta, Advances in Biochemical Engineering/Biotechnology, vol. 63, pp 1-30, 1999].

2.2 AMDase Activity Assay Based on Filter Plate

The bacteria transformed with expression plasmid are plated out on LB-agar which, in addition to the antibiotic carbenicillin, contains 0.2% of arabinose. After culture overnight in an incubator at 37° C., the bacterial colonies are transferred by a stamping method to sterile round paper filters, and these filters are then dried in the air. AMDase-expressing bacterial colonies lead, on incubation of the filters with 20 mM substrate solution (pH 6.0) which contains 0.5 mg/ml of bromothymol blue as a pH indicator, to a change in the colour of the filter areas from yellow (pH 6.0) to blue (pH 8.0), so that the individual colonies can be distinguished according to their enzymatic activity. This system can be used in particular if mutants of AMDase are investigated with regard to their substrate specificity. However, the fine distinction of differences in activity can be performed only inaccurately by this filter plate assay.

2.3 Purification of AMDase

For purification of the AMDase and of the AMDase mutants, the induced bacteria were digested in 20 mM Tris/HCl pH 8.0 (5 ml of buffer/100 ml of culture) by means of ultrasound (15 min 70%, on ice). The cell debris was removed by centrifuging (30 min, 10 000 g) (supernatant corresponds to native extract) and the resulting soluble fraction was purified by NTA affinity chromatography (Qiagen). It was found that the AMDase produced and the various mutants are expressed completely as cytoplasm-soluble protein.

After the inactive fractions had been washed out (with 50 mM imidazole), the active fractions are eluted from the column material with 250 mM of imidazole, purified and subjected to double decomposition against dialysis buffer (10 mM potassium phosphate pH 6.0, 0.1 mM EDTA, 5 mM β-mercaptoethanol). The mutants can be stored dissolved as protein solution at 4° C.

Storage as glycerol solution (1:1 mixtures of the protein solution (in dialysis buffer) with 87% of glycerol) at −20 or −80° C. is likewise possible. It is not necessary to separate off the added glycerol for reaction of the tested substrates.

However, it is also possible to make the whole cells which have expressed AMDase stable with the aid of acetone washes and subsequent drying of the cells, and to isolate the enzyme later on, or to use the whole cells for an enzyme reaction. Stabilization of the cells can also comprise freeze-drying or spray-drying.

EXAMPLE 3

Characterization of the AMDase 3.1 Determination of the Conversion and of the Enantiomeric Excess The determination of the conversion and of the enantiomeric excesses achieved was effected according to known literature data from [Miyamoto, K. & Ohta, H. (1992): Eur. J. Biochem. 210, 475-481].

3.2 Enzyme Kinetics of AMDase

The enzymatic activity of the purified enzyme is checked in a photometric assay. For this purpose, the corresponding substrate was dissolved in water to give a 20 mM solution and was adjusted to pH 6.0 with KOH. 0.05 mg/ml of bromothymol blue was also added to the substrate solution as an indicator. The addition of the AMDase results in a decarboxylation of the substrate, the resulting pH change leads to a colour change of the indicator (yellow [pH 6.0]→blue [pH8]) which can be measured at 615 to 620 nm in the photometer (pH assay). It is sufficient to add 20 µl of an enzyme solution which has an optical density of 0.15 (about 5.5 µg, Bradford test with BSA as reference) to 200 µl of substrate solution.

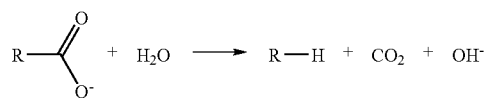

In addition to the phenylmalonic acid, a number of other malonic acid derivatives were also prepared and investigated.

3.3 Reaction of Phenylmalonic Acid with the Use of Whole Cells

For the substrate reaction with whole cells, cells which carry the enzyme-coding plasmid were cultured for 6 h under enzyme-inducing conditions (0.02% arabinose in LB medium). Substrate solution (20 mM phenylmalonic acid pH 6.0, 0.05 mg/ml of bromothymol blue) was added to the induced and sedimented cells and the change in extinction was recorded as a function of time on the photometer.

In the reaction of phenylmalonic acid with whole, AMDase-producing cells, it was found that both cytoplasmic expression and periplasmic expression can be used for reaction of the substrate.

3.4 Reaction of Different Substrates with the Use of AMDase After Periplasmic Expression For the substrate reaction with whole cells, cells which carry the enzyme-coding plasmid, including the N-terminal pelB export sequence, were cultured for 6 h under enzyme-inducing conditions (0.02% arabinose in LB medium). Substrate solution (20 mM phenylmalonic acid pH 6.0, 0.05 mg/ml of bromothymol blue) was added to the induced and sedimented cells and the change in extinction was recorded as a function of time on the photometer (cf. above).

```
N-terminus:
                                    (SEQ ID NO: 6)
PelB                AMDase (wild-type)
MKTLLPTAAAGLLLLAAEPAMAMGQMQQASTPTIGMI . . .
```

The periplasmic protein expression can be verified by means of a periplasm preparation.

EXAMPLE 4

AMDase Mutants Having Improved Activity Compared with the Substrates Known to Date Numerous mutants of AMDase which have improved enzyme activity compared with the substrates known to date from Ohta et al. were produced by mutagenesis. The modified amino acid sequences were verified by sequencing of the expression plasmids. It was found that the exchange of certain amino acids, such as, for example, 17, 19, 22, 24, 25, 32, 41, 42, 47, 53, 60, 61, 63, 68, 74, 84, 85, 87, 94, 103, 112, 119, 121, 139, 142, 155, 168, 173, 178, 199, 201, 203, 205, 207, 210, 221, 222, 223, 224, 225, 226, 227, 228, 229, 230, 231, 232, 238 and/or 240, for alanine or glycine or further amino acids, such as, for example, glutamine or glutamic acid and histidine leads to an improved conversion of α-methylphenylmalonic acid derivatives or of phenylmalonic acid to α-methylphenylacetic acid derivatives or phenylacetic acid. In the mutations, a wild-type alanine was replaced by glycine or glutamine, and glutamic acid or histidine or another amino acid was replaced by alanine or further amino acids.

EXAMPLE 5

AMDase Mutants Having Improved Activity Compared with α-Hydroxy-, α-Thiol- or α-Aminophenylmalonic Acid Derivatives Using α-Hydroxy(4-Methylphenyl) Malonic Acid as an Example Numerous mutants of AMDase which have an improved enzyme activity compared with α-hydroxyphenylmalonic acid derivatives were produced by mutagenesis. The modified amino acid sequences were verified by sequencing of the expression plasmids. It was found that the exchange of certain amino acids, such as, for example, of phenylalanine 85 for alanine (F85A) leads to a conversion of α-hydroxy(4-methylphenyl)malonic acid (KS38) to the corresponding mandelic acid derivative in high yield (94%) and with a high enantiomeric excess (98). It was unimportant whether, for example, the aromatic ring system carries a methyl or an isobutyryl group in the para position (comparison KS38/KS30). However, the introduction of various other mutations, such as, for example, at position 17, 19, 22, 24, 32, 41, 42, 46, 47, 53, 60, 61, 63, 68, 74, 83, 84, 85, 87, 94, 103, 105, 112, 116, 119, 121, 139, 142, 155, 168, 171, 173, 178, 199, 201, 202, 203, 204, 205, 210, 221, 222, 224, 225, 226, 227, 228, 229, 230, 235, 238, 239 and/or 241 (individual mutations as well as double and triple mutations or multiple mutations), also leads to a conversion of α-hydroxyphenylmalonic acid derivatives.

The substrates used have the following structural formulae:

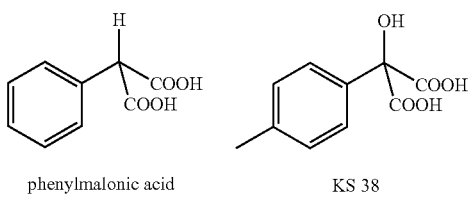

phenylmalonic acid    KS 38

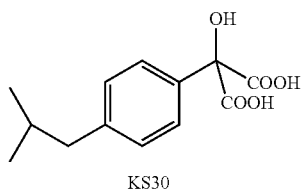

KS30

The corresponding α-methylphenylmalonic acids were prepared by a known synthesis method and were used [Ghosh, S. et al. (1982): J. Org. Chem. 47, 4692-4702]. The starting compounds required for this synthesis route (of the enzymatic decarboxylation) are obtained by reacting an α-ketomalonic ester over tin (IV) chloride with the aryl group to be appropriately introduced.

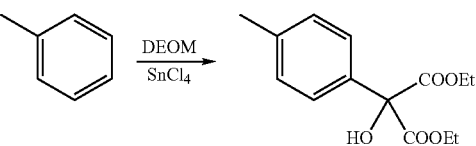

After hydrolysis of the carboxylic ester (chemically or enzymatically), the resulting α-hydroxymalonic acid derivative can be used directly as an enzyme substrate [Miyamoto, K. & Ohta, H. (1991): Biocatalysis 5, 49-60].

Two routes would be conceivable for the enzymatic cleavage of the carboxylic esters. Firstly an upstream hydrolysis of the carboxylic esters with the aid of a pig's liver esterase or of an unspecific hydrolyase [Faber, K. Biotransformations in Organic Chemistry, 4th Ed., Springer-Verlag (2000); Drauz, K., Waldmann, H., Enzyme Catalysis in Organic Synthesis, VCH (1995); Lange et al., Chembiochem. 2, 576-82 (2001)], so that the resulting dicarboxylic acid can then be used for the decarboxylation. However, coexpression of the decarboxylase together with the ester-cleaving enzyme in the same host organism would also be possible; this would then mean that only a one-step reaction process has to be carried out.

The results of the enzymatic decarboxylation are summarized as examples in Table 1.

Summary of Some Results for Phenylmalonic Acid and for KS38 as an Example

TABLE 1

| Position of the mutation | Activity Phenyl-malonic acid (ΔE/min) | Relative improvement phenylmalonic acid | Activity KS38 (ΔE/min) | Relative improvement KS38 |
| --- | --- | --- | --- | --- |
| Wild-type enzyme | 0.0957 | 1 | 0.00162 | 1 |
| A84G | 0.2051 | 2.14 | 0.00323 | 1.99 |
| F85A | 0.1925 | 2.01 | 0.00515 | 3.18 |
| A87G | 0.1477 | 1.54 | 0.00366 | 2.26 |
| R94A | 0.1592 | 1.66 | 0.00371 | 2.29 |
| T103A | 0.1661 | 1.73 | 0.00408 | 2.52 |

TABLE 1-continued

| Position of the mutation | Activity Phenyl-malonic acid (ΔE/min) | Relative improvement phenylmalonic acid | Activity KS38 (ΔE/min) | Relative improvement KS38 |
| --- | --- | --- | --- | --- |
| I127A | 0.1850 | 1.93 | 0.00410 | 2.53 |
| F85A, R173A | 0.1361 | 1.42 | 0.00508 | 3.14 |
| F85A, E176A | 0.1091 | 1.14 | 0.00520 | 3.21 |
| F85A, A178G | 0.1134 | 1.18 | 0.00653 | 4.03 |

In the first column of Table 1, under the heading "Position of the mutation", the localization of the mutation is given. The first uppercase letter indicates the amino acid in the wild-type sequence at the position which is characterized by the following number (e.g. 84). The second uppercase letter indicates the amino acid which was inserted in the mutants instead of the wild-type amino acid. Thus, for example "A84G" means that the alanine of the wild-type sequence at position 84 was replaced by a glycine in the mutant sequence. A plurality of such data means that the sequence has a plurality of mutations; thus, the last three lines of Table I describe double mutations.

EXAMPLE 6

AMDase Mutants Having Improved Stability Compared with Chemical or Thermal Denaturing Numerous mutants of AMDase which have higher stability compared with chemical or thermal denaturing were produced by mutagenesis. The modified amino acid sequences were verified by sequencing of the expression plasmids. It was found that the exchange of certain amino acids, such as, for example, of P15 for alanine (P15A), and the exchange of G74 for alanine (G74A) and D128 for alanine (D128A), leads to a substantial physical stabilization of the enzyme.

Comparison of Some Mutants of AMDase which have been Stabilized by Mutagenesis

TABLE 2

Residual activity of the wild-type protein and of some newly generated mutants after incubation at 50° C. for 35 min (10 mM potassium phosphate pH 6.0, 0.1 mM EDTA, 5 mM βmercaptoethanol). The activity was subsequently investigated in comparison with the untreated enzyme on the basis of the conversion of phenylmalonic acid (20 mM pH 6.0). The mutants shown here are: P15A, P32A, G74A, T75A, D128A, D163A, A165G and C171A.

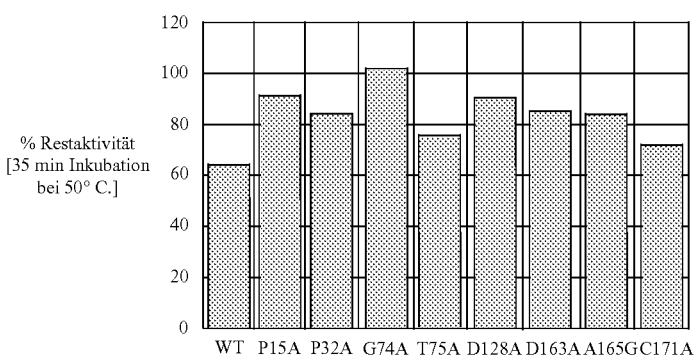

% Restaktivität [35 min Inkubation bei 50° C.] = % residual activity [35 min incubation at 50° C.].

EXAMPLE 7

Documentation of the Various Levels of Expression

In order to demonstrate that the mutations of the present invention cannot be directly determined using routine methods, DNA sequences which were optimized using commercially available programs were compared with the sequences optimized according to the invention.

In the experiment, E. coli Top 10 cells were transfected with pBADHisA plasmids which had different sequences. One sequence reproduced as sequence ID No. 7, was optimized using the commercially available program DNA-Star. The other sequence with the sequence ID No. 8 was obtained according to the invention. These sequences were introduced into the transfected E. coli cells.

After transfection, five individual clones were identified from the plates, which were transformed with the sequence (sequence ID No. 7) optimized using the commercial program DNA-Star, and these clones were cultured. *E. coli* cells were likewise transfected with the sequence ID No. 8 according to the invention, and four transfected clones were randomly selected.

These clones, designated by K1-K5 (DNA-Star) or K6-K9 (according to the invention) were cultured on a small scale and induced with 0.02% arabinose after 6 hours. Thereafter, the cells were pelletized, lysed in sample buffer and separated on an SDS-polyacrylamide gel (12.5%).

An image of the gel is shown in FIG. 3. Polyacrylamide gel clearly shows that, under the same conditions, considerably more protein was produced in the case of clones K6-K9 (sequence according to the invention) (cf. arrow) than in the case of the clones K1-K5 (optimized with DNA-Star).

This increase in expression makes a process in which the enzyme is to be used on an industrial scale considerably more advantageous.

The right column of FIG. 3 shows a size marker with proteins of the following size: 116, 66.2; 45; 35, 25; 18, 4 and 14.4 kD. The size of the protein investigated is about 26.3 kD.

SEQUENCE LISTING

```
<160> NUMBER OF SEQ ID NOS: 6

<210> SEQ ID NO 1
<211> LENGTH: 250
<212> TYPE: PRT
<213> ORGANISM: Alcaligenes bronchisepticus

<400> SEQUENCE: 1

Met Gln Gln Ala Ser Thr Pro Thr Ile Gly Met Ile Val Pro Pro Ala
 1               5                  10                  15

Ala Gly Leu Val Pro Ala Asp Gly Ala Arg Leu Tyr Pro Asp Leu Pro
            20                  25                  30

Phe Ile Ala Ser Gly Leu Gly Leu Gly Ser Val Thr Pro Glu Gly Tyr
        35                  40                  45

Asp Ala Val Ile Glu Ser Val Val Asp His Ala Arg Arg Leu Gln Lys
    50                  55                  60

Gln Gly Ala Ala Val Val Ser Leu Met Gly Thr Ser Leu Ser Phe Tyr
65                  70                  75                  80

Arg Gly Ala Ala Phe Asn Ala Ala Leu Thr Val Ala Met Arg Glu Ala
                85                  90                  95

Thr Gly Leu Pro Cys Thr Thr Met Ser Thr Ala Val Leu Asn Gly Leu
            100                 105                 110

Arg Ala Leu Gly Val Arg Arg Val Ala Leu Ala Thr Ala Tyr Ile Asp
        115                 120                 125

Asp Val Asn Glu Arg Leu Ala Ala Phe Leu Ala Glu Glu Ser Leu Val
    130                 135                 140

Pro Thr Gly Cys Arg Ser Leu Gly Ile Thr Gly Val Glu Ala Met Ala
145                 150                 155                 160

Arg Val Asp Thr Ala Thr Leu Val Asp Leu Cys Val Arg Ala Phe Glu
                165                 170                 175

Ala Ala Pro Asp Ser Asp Gly Ile Leu Leu Ser Cys Gly Gly Leu Leu
            180                 185                 190

Thr Leu Asp Ala Ile Pro Glu Val Glu Arg Arg Leu Gly Val Pro Val
        195                 200                 205

Val Ser Ser Pro Ala Gly Phe Trp Asp Ala Val Arg Leu Ala Gly
    210                 215                 220

Gly Gly Ala Lys Ala Arg Pro Gly Tyr Gly Arg Leu Phe Asp Glu Ser
225                 230                 235                 240

Gly Gly Ser His His His His His Ala
                245                 250

<210> SEQ ID NO 2
<211> LENGTH: 769
<212> TYPE: DNA
<213> ORGANISM: Artificial Sequence
<220> FEATURE:
```

<223> OTHER INFORMATION: Alcaligenes bronchisepticus

<400> SEQUENCE: 2

| | | | | | |
|---|---|---|---|---|---|
| ccatgggcca | aatgcaacag | gcaagcaccc | cgaccattgg | tatgatcgta | cctcccgcag | 60 |
| ctggactagt | gccagccgac | ggcgctcgtc | tgtatccgga | tttgccgttt | atcgcgtcgg | 120 |
| gtttgggcct | gggatccgtg | actcccgaag | gctatgacgc | ggttatagaa | agcgtggttg | 180 |
| atcatgctcg | tcgcctgcaa | aaacaggggg | cagccgttgt | gtctctcatg | ggtacctcct | 240 |
| tgtcgttcta | ccgcggcgcc | gcttttaacg | cggcgctgac | tgtcgccatg | cgtgaggcta | 300 |
| ctggcctgcc | gtgtactacc | atgagtaccg | ccgtgctaaa | cggcctgcgt | gcactgggcg | 360 |
| tccggcgtgt | ggcactggcg | accgcctata | tcgatgatgt | taatgaacgg | cttgcagcgt | 420 |
| ttctggcgga | agaatccctg | gtaccgacag | gttgtcgtag | cttaggcatt | accggagtag | 480 |
| aagcgatggc | tcgagtggat | accgccactc | tggtcgatct | gtgcgtccgc | gcctttgaag | 540 |
| cagcaccaga | tagcgatggg | attctgttgt | cgtgtggcgg | tctgcttacc | ttggacgcaa | 600 |
| tcccggaagt | cgagcgtcgc | ctgggtgtgc | cagtcgtctc | aagcagtccg | gcgggctttt | 660 |
| gggatgcggt | ccgtttggct | ggcggaggcg | ccaaagcacg | cccgggttac | ggccggcttt | 720 |
| ttgatgagtc | cggtggcagc | caccatcacc | atcaccatta | agcttagca | | 769 |

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3

| | |
|---|---|
| ccggaattcc catgggccaa | 20 |

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4

| | |
|---|---|
| caccatcacc atcaccatta agctt | 25 |

<210> SEQ ID NO 5
<211> LENGTH: 729
<212> TYPE: DNA
<213> ORGANISM: Alcaligenes bronchisepticus

<400> SEQUENCE: 5

| | | | | | |
|---|---|---|---|---|---|
| atgcaacagg | caagcacccc | gaccattggt | atgatcgtac | ctcccgcagc | tggactagtg | 60 |
| ccagccgacg | gcgctcgtct | gtatccggat | ttgccgttta | tcgcgtcggg | tttgggcctg | 120 |
| ggatccgtga | ctcccgaagg | ctatgacgcg | gttatagaaa | gcgtggttga | tcatgctcgt | 180 |
| cgcctgcaaa | aacaggggc | agccgttgtg | tctctcatgg | gtacctcctt | gtcgttctac | 240 |
| cgcggcgccg | cttttaacgc | ggcgctgact | gtcgccatgc | gtgaggctac | tggcctgccg | 300 |
| tgtactacca | tgagtaccgc | cgtgctaaac | ggcctgcgtg | cactgggcgt | ccggcgtgtg | 360 |
| gcactggcga | ccgcctatat | cgatgatgtt | aatgaacggc | ttgcagcgtt | tctggcggaa | 420 |
| gaatccctgg | taccgacagg | ttgtcgtagc | ttaggcatta | ccggagtaga | agcgatggct | 480 |
| cgagtggata | ccgccactct | ggtcgatctg | tgcgtccgcg | cctttgaagc | agcaccagat | 540 |

```
agcgatggga ttctgttgtc gtgtggcggt ctgcttacct tggacgcaat cccggaagtc    600
gagcgtcgcc tgggtgtgcc agtcgtctca agcagtccgg cgggcttttg ggatgcggtc    660
cgtttggctg gcggaggcgc caaagcacgc ccgggttacg gccggctttt tgatgagtcc    720
ggtggcagc                                                           729

<210> SEQ ID NO 6
<211> LENGTH: 37
<212> TYPE: PRT
<213> ORGANISM: Artificial Sequence
<220> FEATURE:
<223> OTHER INFORMATION: Completely synthesized construct

<400> SEQUENCE: 6

Met Lys Thr Leu Leu Pro Thr Ala Ala Ala Gly Leu Leu Leu Leu Ala
1               5                   10                  15

Ala Glu Pro Ala Met Ala Met Gly Gln Met Gln Gln Ala Ser Thr Pro
                20                  25                  30

Thr Ile Gly Met Ile
            35
```

The invention claimed is:

1. A process for the stereoselective decarboxylation of malonic acid derivatives of the formula (I)

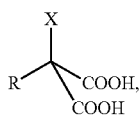

(I)

the process comprising:
using a decarboxylase to produce a compound of the formula (II)

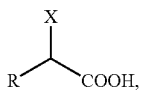

(II)

wherein X is selected from the group consisting of OH, SH, $C_2$-$C_{10}$ alkyl, $C_1$-$C_{10}$ alkoxy, and $NH_2$, and R is selected from the group consisting of aryl, heteroaryl, condensed aryl, and condensed heteroaryl radical, wherein R is substituted or unsubstituted, and optionally wherein a substituent is selected from the group consisting of a halogen, alkyl, alkenyl, and alkynyl radical;

wherein said decarboxylase comprises the amino acid sequence of SEQ ID NO: 1, except for a mutation at an amino acid position of SEQ ID NO: 1 selected from the group consisting of 15, 17, 19, 22, 24, 25, 32, 41, 42, 46, 47, 53, 60, 61, 63, 68, 74, 75, 83, 84, 85, 87, 94, 103, 105, 112, 116, 119, 121, 128, 139, 142, 155, 163, 165, 168, 173, 178, 199, 201, 202, 203, 204, 205, 210, 221, 222, 224, 225, 226, 227, 228, 229, 230, 235, 238, 239, 240, and combinations thereof;

wherein said mutation comprises replacing the amino acid at said position with any other amino acid, wherein, at position 188, the cysteine residue is not replaced, and wherein not more than 10 amino acids are inserted into and/or deleted from the sequence according to SEQ ID NO: 1.

2. The process according to claim 1, wherein said decarboxylase comprises a mutation at an amino acid position of SEQ ID NO: 1 selected from the group consisting of 17, 19, 24, 32, 41, 42, 46, 47, 53, 60, 61, 63, 68, 74, 84, 85, 87, 94, 103, 116, 119, 142, 199, 202, 210, 225, 229, 230, 238, and combinations thereof.

3. The process according to claim 1, wherein said decarboxylase comprises a mutation at an amino acid position of SEQ ID NO: 1 selected from the group consisting of 19, 24, 32, 42, 46, 47, 60, 61, 63, 68, 84, 85, 103, 199, 202, and combinations thereof.

4. The process according to claim 1, wherein said at least one mutation improves the thermal stability of the decarboxylase, and wherein said mutation is replacement of the amino acid at a position of SEQ ID NO: 1 selected from the group consisting of 15, 32, 74, 75, 128, 163, 165, and combinations thereof.

5. The process according to claim 1, wherein said decarboxylase is able to convert malonic acid derivatives of the formula III

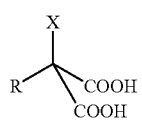

(III)

into a compound of the Formula (IV)

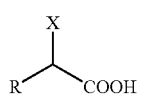

(IV)

wherein X is selected from the group consisting of F, $CH_3$, and H, and R is selected from the group consisting of aryl, heteroaryl, condensed aryl, and condensed heteroaryl radical, wherein R is substituted or unsubstituted, and optionally wherein a substituent is selected from the group consisting of a halogen, alkyl, alkenyl, and alkynyl radical.

6. The process according to claim 5, wherein the compound of the Formula (II) has the R-configuration.

7. The process according to claim 1, wherein the decarboxylase comprises a polyhistidine sequence of amino acids at the C-terminus and/or at the N-terminus.

* * * * *